United States Patent
Magnusson et al.

(10) Patent No.: US 9,333,056 B2
(45) Date of Patent: May 10, 2016

(54) DENTAL COMPONENT AND A DENTAL IMPLANT

(75) Inventors: Daniel Magnusson, Hönö (SE); Josef Saltell, Göteborg (SE)

(73) Assignee: DENTSPLY International Inc., York, PA (US)

( * ) Notice: Subject to any disclaimer, the term of this patent is extended or adjusted under 35 U.S.C. 154(b) by 0 days.

(21) Appl. No.: 13/613,118

(22) Filed: Sep. 13, 2012

(65) Prior Publication Data

US 2013/0244204 A1  Sep. 19, 2013

Related U.S. Application Data

(60) Provisional application No. 61/534,521, filed on Sep. 14, 2011.

(30) Foreign Application Priority Data

Sep. 14, 2011  (EP) .................................... 11181242

(51) Int. Cl.
  *A61C 8/00*  (2006.01)
(52) U.S. Cl.
  CPC ............. *A61C 8/0066* (2013.01); *A61C 8/0054* (2013.01); *A61C 8/0068* (2013.01); *A61C 8/0069* (2013.01); *A61C 8/0089* (2013.01); *A61C 8/0001* (2013.01); *A61C 8/008* (2013.01); *A61C 2008/0046* (2013.01)
(58) Field of Classification Search
  CPC .. A61C 8/0066; A61C 8/0068; A61C 8/0069; A61C 8/0089; A61C 8/0001; A61C 8/0054; A61C 8/0089; A61C 8/0001; A61C 8/008

USPC ......................................... 433/172–176, 201.1
See application file for complete search history.

(56) References Cited

U.S. PATENT DOCUMENTS

| | | | |
|---|---|---|---|
| 6,116,904 A | 9/2000 | Kirsch et al. | |
| 6,227,859 B1 | 5/2001 | Sutter | |
| 6,332,777 B1 | 12/2001 | Sutter | |
| 6,382,977 B1 | 5/2002 | Kumar | |
| 6,461,160 B1 | 10/2002 | Sutter | |
| 6,726,480 B1 | 4/2004 | Sutter | |
| 7,104,797 B2 * | 9/2006 | Rassoli | 433/173 |
| 7,108,510 B2 | 9/2006 | Niznick | |
| 2003/0148246 A1 * | 8/2003 | Lustig et al. | 433/172 |

(Continued)

FOREIGN PATENT DOCUMENTS

| | | |
|---|---|---|
| EP | 1444964 A2 | 5/1998 |
| WO | 0105326 A1 | 1/2001 |
| WO | 0128451 A1 | 4/2001 |
| WO | 2005058178 A2 | 6/2005 |
| WO | 2009149881 A1 | 12/2009 |
| WO | 2011023750 A2 | 3/2011 |

OTHER PUBLICATIONS

International Search Report, Application No. 2012/0676432, Search completed Dec. 19, 2012.

(Continued)

*Primary Examiner* — Edward Moran
(74) *Attorney, Agent, or Firm* — David A. Zdurne; Douglas J. Hura; Leana Levin (57) ABSTRACT

A dental component having a first indexing element and at least two second indexing elements having apical ends located apically of the apical end of said first indexing element.

11 Claims, 5 Drawing Sheets

(56) References Cited

U.S. PATENT DOCUMENTS

| | | |
|---|---|---|
| 2005/0065525 A1 | 3/2005 | Aringskog et al. |
| 2005/0136380 A1 | 6/2005 | Niznick |
| 2007/0059666 A1 | 3/2007 | Zickman |
| 2007/0281278 A1* | 12/2007 | Jorneus et al. ............ 433/173 |
| 2008/0096168 A1 | 4/2008 | Schonenberger |
| 2009/0035721 A1* | 2/2009 | Garcia Saban et al. ....... 433/174 |
| 2009/0123890 A1 | 5/2009 | Purga et al. |
| 2010/0184002 A1* | 7/2010 | Ranck et al. ................ 433/172 |

OTHER PUBLICATIONS

International Written Opinion, Application No. 2012/067642, Mail date Jan. 7, 2013.

European Search Report, application No. 11181242.6, Search completed Jun. 22, 2012.

* cited by examiner

DENTAL COMPONENT AND A DENTAL IMPLANT

RELATED APPLICATIONS

This patent application claims the benefit of and priority to EP Application Ser No. 11181242.6, filed on Sep. 14, 2011 and U.S. Provisional Patent Application Ser. No. 61/534,521, filed on Sep. 14, 2011, which are herein incorporated by reference for all purposes.

TECHNICAL FIELD

The present invention relates to a dental component comprising a fixture engagement portion for engaging the dental component with a dental fixture adapted to be inserted into a jawbone or for engaging the dental component with a fixture replica. The invention also relates to a dental implant comprising a dental fixture adapted to be inserted into a jawbone and a dental component connectible to the dental fixture. The invention also relates to such a dental fixture.

BACKGROUND OF THE INVENTION

Dental implant systems are widely used for replacing damaged or lost natural teeth. In such systems, a dental fixture is placed in the jawbone of a patient in order to replace the natural tooth root. An abutment structure comprising one or several parts may then be attached to the fixture in order to build up a core for the part of the prosthetic tooth protruding from the bone tissue, through the soft gingival tissue and into the mouth of the patient. On said abutment, the prosthesis or crown may finally be seated.

The final prosthesis should be sized and configured so as to naturally fit with the remaining teeth of the patient, both for functionality and aesthetics. To this end a dental technician may try out a proper prosthesis for the individual patient, using a model of the jaw of the patient, said model including the fixture. The dental technician may also digitally work out a proper prosthesis based on a digital model of the jaw of the patient either with a fixture already installed or prior to such installation. The dental technician may also modify a prefabricated abutment to match the contour of the soft gingival tissue.

There are various fixture configurations. For instance, a fixture may have a flat topped coronal head portion, which may be installed in any rotational position relative to the jawbone. Another type of fixture configuration is a fixture having a sloped coronal end portion, such as disclosed in U.S. Pat. No. 6,655,961, in which the length of the fixture is greater on the lingual side than on the buccal side in order to match the contour of the jawbone.

Similarly, to the above described fixture/jawbone-interface, for a superstructure, such as an abutment, there may be an abutment/fixture-interface in which the abutment should only be positioned in one way relative to the fixture, e.g. an abutment having a sloped portion matching the sloped head portion of a fixture. This is one type of asymmetrical superstructure, in which the asymmetrical feature should be positioned in a desired rotational relationship to either or both of the fixture and the jawbone with surrounding teeth. Thus, with regard to these interfaces, it would be desirable to ensure that the dentist connects the superstructure with a correct rotational orientation relative to certain fixtures or jawbone features. Also for patient-specific or customized superstructures, such as a customized abutment, such superstructure may often be made with a certain intended rotational orientation relative to the fixture and surrounding contours. Thus, also in these cases it would be desirable to ensure that the dentist connects the superstructure with a correct rotational orientation relative to the fixture and other features in the oral cavity.

When making an abutment and a prosthetic tooth, the dental technician has thus taken the contours and locations of surrounding tissue and adjacent teeth into account. A system used at present time to manoeuvre the rotational position of asymmetrical superstructures is to provide a two-part abutment having a centrally positioned threaded screw, which mates with an internally threaded bore of the fixture, and a sleeve which is given the asymmetrical patient specific features at its coronal end which are needed to be a suitable basis for the prosthetic tooth. The sleeve may be rotated into the correct position in a seating of the internal bore of the fixture and be fixed therein by the screw. The seating in the fixture and the apical end of the sleeve of the abutment are axially symmetrical to ensure that a correct final position may be achieved. The correct positioning is this way depending on the dentist's ability to visually verify the result.

The dentist receives the abutment and prosthetic tooth either as one integral unit or as separate parts to be assembled in the oral cavity of the patient. Often, the dentist who receives the abutment and the prosthetic tooth should understand how the abutment should be rotationally oriented relative to the fixture in order to obtain the alignment as intended by the dental technician. Nevertheless, it may sometimes be difficult for the dentist to see which is the correct orientation and, of course, there may be a risk of the dentist simply overlooking or ignoring the correct rotational orientation of the abutment relative to the fixture.

There have been proposed different solutions which only allow the abutment to be placed in a single rotational orientation relative to the fixture. Nevertheless, dentists may still experience difficulties in finding the correct orientation, and may have to rotate the abutment for a while before it falls into place.

An object of the invention is to enable the dentists to find a desired rotational orientation of a dental component, such as an abutment, relative to a fixture more easily than what is offered by the currently available solutions.

These and other objectives, which will become apparent in the following, are achieved by the dental component and the dental implant as defined in the accompanied claims.

SUMMARY OF THE INVENTION

The present invention is based on the insight that when connecting a dental component to a dental fixture, two or more leading indexing elements may be used for guiding the dental component into a desired rotational position relative to the fixture before one or more subsequent trailing indexing elements are engaged to form the final rotational lock.

According to a first aspect of the invention, a dental component is provided. The dental component comprises a fixture engagement portion for engaging the dental component with a dental fixture adapted to be inserted into a jawbone or for engaging the dental component with a fixture replica, the fixture engagement portion having a geometrical central axis and being provided with at least one radially projecting first indexing element having an apical end, and at least two radially projecting second indexing elements, each one having an apical end located apically of the apical end of said first indexing element.

This has the effect that when the dental component is to be connected with the fixture and thus moved towards the fixture, the at least two second indexing elements will be the first to mate with the fixture. In this way, the location finding function of the indexing elements will be concentrated to only part of the circumference of the fixture engagement portion. The dentist will experience a more distinct perception when said at least two second indexing elements fall into place with a corresponding receiving portion of the fixture, compared to if all indexing elements around the circumference of the fixture engagement portion were to connect simultaneously as in the prior art.

According to at least one example embodiment, said at least two second indexing elements are asymmetrically distributed along the circumference of the fixture engagement portion. Since the second indexing elements are asymmetrically distributed along the circumference of the fixture engagement portion, a component/fixture interface may, if desired, be provided in which the second indexing elements only have one correct rotational position, thereby avoiding that the dentist connects the dental component to the fixture in an incorrect rotational orientation.

According to at least one example embodiment, said at least one first indexing element is circumferentially separated from any one of said at least two second indexing elements This means that said first indexing element is located at a different position along the circumference of the fixture engagement portion than any one of the second indexing elements. In other words, a radius drawn from the geometrical central axis to the first indexing element extends in a different direction from said axis than any radii drawn from said axis to the second indexing elements.

Suitably, the apical ends of said at least two second indexing elements are arranged at substantially the same level in the apical-coronal direction.

Having at least two second indexing elements with a leading function achieves a stabilizing or balancing effect. If the dental component is intended to be connected to a dental fixture allowing the dental component to be arranged in any one of a plurality of rotational orientations, it can be connected in any one of those rotational orientations. However, when the dentist wishes to connect the dental component to a dental fixture only allowing the dental component to be connected in a single specified rotational orientation, the advantage of having two leading second indexing elements will become apparent. If there would have been only one leading second indexing element it could have incorrectly be received by anyone of the mating (suitably indented) indexing elements of the fixture, before the dentist annoyed realizes the incorrect rotational orientation because of the trailing first indexing element does not find a mating indexing element. By having two leading second indexing elements, only when both have been aligned with the correct indexing elements of the fixture will the mating be possible. As long as one of the second indexing elements rests on a surrounding wall portion (e.g. a shelf) in the fixture, it prevents the dental component from moving further apically, and thus also prevents the other second indexing element from dropping into an incorrect indentation in the fixture.

According to at least one example embodiment, the axial extension of the indexing elements is such that the first indexing element and the second indexing elements are intersected by a common geometrical plane which is perpendicular to the central axis of the fixture engagement portion. Thus, apart from having the apical ends located at different apical positions, the first and second indexing elements may have substantially the same configuration which may be advantageous from a manufacturing perspective. Furthermore, although the dental component may only have one specific rotational orientation in one type of fixture, it could be allowed to have other rotational orientations in other types of fixtures, in which case the mating indexing elements in the fixture could receive any one of the first and second indexing elements of the dental component. Such freedom of choice would be more complicated if the first and second indexing elements are completely separated in the axial direction of the fixture engagement portion.

According to at least one example embodiment, said at least one radially projecting first indexing elements comprises at least two radially projecting first indexing elements. Thus, in such case, there will be at least two leading (second) indexing elements which will facilitate finding the correct location and at least two trailing (first) indexing elements which will provide and/or complement a rotational locking of the dental component to the fixture.

According to at least one example embodiment, said at least two radially projecting second indexing elements are arranged as at least three radially projecting second indexing elements, interposed between two of said first indexing elements, wherein each one of said at least three second indexing elements has an apical end which is located apically of the apical ends of said first indexing elements. This provides increased stability when the dentist intends to find of the correct rotational orientation of the dental component in the fixture.

Thus, it should be understood that said at least two second indexing element may, for instance, be three, four or more indexing elements.

According to at least one example embodiment, a radius from said central axis to the centre of one of said at least two second indexing elements and a radius from said central axis to the centre of said first indexing element form a first angle, wherein a radius from said central axis to another one of said at least two second indexing elements and said radius from said central axis to the centre of said first indexing element form a second angle, wherein said second angle is different from said first angle and from any angle being a multiple of said first angle. A multiple is the product of a quantity by an integer. In other words, $\phi \neq n\theta$, where $\theta$ is the first angle, $\phi$ is the second angle and n is a positive integer.

Since said second angle is different from said first angle (and any multiple thereof) an asymmetry is achieved. Only by rotating the dental component a full 360° can the first and second indexing elements obtain the same positional distribution relative to the surrounding environment. This is in contrast to a symmetrical distribution of indexing elements; for instance, a component having four symmetrically distributed indexing elements can be rotated 90° to obtain the same positional distribution as before relative to the surrounding environment. The asymmetry provided by this example embodiment reduces the risk of the second indexing elements getting caught in incorrect indexing elements in the fixture.

The asymmetrical distribution of the indexing elements comprising at least two first and at least two second indexing elements is reflected in at least one example embodiment, according to which the spacing between said two second indexing elements is different from the spacing between any two of said first indexing elements. The two second indexing elements do not have to lie next to each other. There may be one or more first indexing elements which are placed between said two second indexing element. Also, if there are more than two second indexing elements, some of them may be spaced at the same distance as the spacing between first indexing elements, as long as there can be identified one pair of second indexing elements having a different spacing. The advantage of this asymmetry will now be explained. Assuming the dental component is to be connected to a dental fixture having corresponding mating third and fourth indexing elements, wherein the third indexing elements are designated to mate with the first indexing elements of the dental component while the fourth indexing elements are designated to mate with the second indexing elements of the dental component, then there will be only one correct rotational orientation. Since the apical ends of the second indexing elements will be leading and be the first to form contact with the dental fixture, because of the distinct spacing between said pair of second indexing elements these cannot inadvertently be mated with the differently spaced third indexing elements.

According to at least one example embodiment said at least one first indexing element and said at least two second indexing elements together form a series of indexing elements which comprises the following two classifications:

Classification A: Indexing elements which are separated from their neighboring indexing elements by no more than a first distance.

Classification B: Indexing elements that are separated from their neighboring indexing elements by more than said first distance, wherein at least one of the second indexing elements is present in Classification A.

For instance, indexing elements under Classification B may be distributed around the fixture engagement portion at intervals of an angle θ, and an indexing element under Classification A would be interposed between the other indexing elements. As an example, there may be six indexing elements which are spaced at 60° intervals from one indexing element to the next, and a seventh indexing element which is located in-between two of the other six elements (i.e. spaced at 30° from those two indexing elements). Said six regularly distributed indexing elements could go under classification B, however, out of those six indexing elements, the two indexing elements neighboring the seventh indexing element could also go under Classification A (as would the seventh indexing element). Thus, at least the extra seventh indexing element is in the form of one of said at least one second indexing elements having an apical end located apically of the apical ends of the first indexing element. However, if the mating fixture has seven receiving recesses of substantially equal dimensions, the seventh indexing element could incorrectly enter anyone of those recesses. Therefore, in order to make sure that there is only one rotational orientation in which the dental component can mate with the fixture, at least one of the other six indexing elements should also be a "second" indexing element having an apical end located apically of the apical ends of the first indexing elements. Advantageously, although not necessarily, the two indexing elements which neighbor the seventh indexing element may be "second" indexing elements having an apical end located apically of the apical ends of the first indexing elements.

The above example of the six equidistantly spaced indexing elements, and a seventh extra indexing element is encompassed by at least the following example embodiments. According to at least one example embodiment, said at least one first indexing element and said at least two second indexing elements add up to N number of indexing elements, wherein N−1 of the indexing elements are equidistantly distributed around the fixture engagement portion, and wherein the remaining indexing element (the N:th indexing element) is interposed between two of said equidistantly distributed N−1 indexing elements, wherein the remaining indexing element is one of said at least two second indexing elements. At least one of said equidistantly distributed N−1 indexing elements is also a second indexing element having its apical end located apically of the other equidistantly distributed (first) indexing elements. According to at least one example embodiment, one or both of the indexing elements neighboring said remaining indexing element is/are also a second indexing element.

According to at least one example embodiment, following the circumferential direction of the fixture engagement portion, said at least two second indexing elements are interposed between two of said first indexing elements. Thus, there is at least one geometrical plane which is perpendicular to the central axis of the fixture engagement portion and which extends through the first indexing elements as well as through the second indexing elements. The coronal extension of the second indexing elements may suitably be to the same axial level as the coronal extension of the first indexing elements. Alternatively, the coronal extension of the second indexing elements may be longer or shorter than the coronal extension of the first indexing elements.

In order for the second indexing elements to perform a guiding or leading function and the trailing first indexing element to follow with a final rotational locking function, it is not necessary for the second indexing element to be interposed between two first indexing elements. The entire second indexing element may be located apically of the apical end of the at least one first indexing element. For instance, the second indexing elements may be in the form of short protrusions at an apical sub-portion of the fixture engagement portion, while the apical end of the at least one first indexing element is located coronally thereof, at a coronal sub-portion of the fixture engagement portion. Once the second indexing elements have engaged with matching indexing elements in the fixture, the dental component will continue its relative movement towards the fixture and eventually the at least one first indexing element will also engage a matching indexing element (it is assumed that the indexing elements in the fixture receiving the leading second indexing elements are long enough to allow said continued motion of the dental component). Thus, in view of the above discussion, according to at least one example embodiment, there is at least one geometrical plane which is perpendicular to the central axis of the fixture engagement portion and which is located apically of the at least one first indexing element and coronally of the second indexing elements.

According to at least one example embodiment, the fixture engagement portion of the dental component comprises a cylindrical surface from which said at least one first indexing element and said at least two second indexing elements project radially. This is advantageous from a manufacturing point of view. However, it is conceivable to have the indexing elements project radially from other surfaces as well, e.g. from a tapered surface.

According to at least one example embodiment, the number of first indexing elements is greater than the number of second indexing elements. While the number of second indexing elements may suitably be two or three, the trailing first indexing elements which complete the rotational locking may suitably be more for increased strength. This may be particularly advantageous if the dental component is a driver, wherein the indexing elements are adapted to transfer a torque to the dental fixture when driving it into the jawbone.

According to at least one example embodiment, the apical end of at least one of said at least two second indexing elements is provided with a chamfer. When the fixture engagement portion of the dental component is inserted into the fixture, the dentist will rotate the dental component in order to align the indexing elements of the dental component with mating indexing elements of the fixture. The provision of the two second indexing elements, at least partly reduces the risk of one of those indexing elements engaging with the wrong indexing element in the fixture. Nevertheless, if for instance the dentist tilts the dental component when trying to connect it to the dental fixture, a second indexing element might accidently drops into the wrong indexing element (such as a groove) in the dental fixture upon rotation of the dental component, despite the supporting function of the other second indexing element. In such case, when the dentist continues to apply a rotating force onto the dental component the provision of a chamfer on that second indexing element will facilitate lifting that second indexing element out of the temporary incorrect engagement.

According to at least one example embodiment, each one of said second indexing elements has a smaller dimension in the circumferential (transverse) direction and/or in the radial (projecting) direction compared to the dimensions of said at least one first indexing element. This is advantageous if, for instance the dental fixture has equally dimensioned recesses for receiving the indexing elements (projections) of the dental component, because in such case the second indexing elements, which have a smaller dimension (e.g. transverse to the coronal-apical direction) than the at least one first indexing element, will be received in their receiving recesses with a relatively large play (in this example, a large play in the transverse direction). The second indexing elements, having their apical ends located apically of the apical end of the at least one first indexing element, will be received by their corresponding recess before the trailing first indexing element is received by its corresponding recess in the fixture. The relatively large play facilitates for the dentist to get the second indexing elements into engagement with the corresponding recesses in the fixture. Thus, at this stage, when only the second indexing elements have been engaged, a small rotational movement of the dental component relative to the fixture may be possible. However, when the at least one first indexing element follows to engage with its corresponding recess, since it is suitably more accurately dimensioned to fit closely in its recess, the dental component will become rotationally locked when the one or more first indexing elements have entered in engagement with their respective recesses.

According to at least one example embodiment said at least one first indexing element and said at least one second indexing elements have an elongate extension in the coronal-apical direction. This provides additional strength to the rotational lock compared to if the radially projecting indexing elements would have a shorter extension.

According to at least one example embodiment, the dental component is a component selected from the group consisting of an abutment, an abutment replica, an abutment blank, a customized abutment, a scan abutment, a digital transfer coping, an impression pick-up element, a healing cap and a driver.

For instance, a customized abutment may have a shape which is adapted to the contours of the surrounding tissue and teeth of the patient, in which case it is advantageous if the dentist can easily fit the customized abutment in the intended rotational orientation.

A digital transfer coping having some distinguishing feature indicating its rotational orientation and being connected to a dental fixture may be scanned, and a digital file is then sent to an abutment manufacturer. The digital file will contain information about the position and orientation of the distinguishing feature and thus also the position and orientation of the dental fixture.

A driver having a distinctive marking may be used as an indication to determine if the fixture has been inserted at a desired orientation relative to the jawbone and other surrounding features in the oral cavity. For instance, the fixture may have a sloping coronal end. The driver may be intended to be inserted such that the distinctive marking is aligned with the very top of the sloping end of the fixture. Thus, during rotation of the fixture into the jawbone, the dentist will know the rotational orientation of the fixture and its sloping end by looking at the distinctive marking. It is therefore advantageous if the dentist can easily fit the driver into the intended position relative to the fixture.

According to a second aspect of the invention, a dental implant is provided. The dental implant comprises a dental component comprising a fixture engagement portion provided with at least one first indexing element having an apical end, and at least two second indexing elements, each one having an apical end, a dental fixture adapted to be inserted into a jawbone and comprising a component engagement portion adapted to mate with said fixture engagement portion, the component engagement portion being provided with at least one third indexing element having a coronal end, and at two fourth indexing elements, each one having a coronal end, wherein the apical ends of said at least two second indexing element are located apically of the apical end of the first indexing element and/or the coronal ends of said at least two fourth indexing elements are located coronally of the coronal end of the third indexing element, wherein the first, second, third and fourth indexing elements are distributed along the circumference of the fixture engagement portion and the component engagement portion, respectively, in such way that the dental component can only mate in one rotational orientation with respect to the dental fixture, wherein the first indexing element is only enabled to mate with the third indexing element after said at least two second indexing elements have mated with said at least two fourth indexing elements.

Thus, the second and fourth indexing elements will act to guide the dental component into a desired rotational orientation relative to the fixture. Once this rotational orientation has been found, and the dental component is continued to be displaced apically, the first and third indexing element will then engage each other to provide a final rotational stop. While the first and third indexing elements, suitably, form a relatively tight fit in order to reduce the risk of small rotational movements between the dental component and the dental fixture, the fit between the second and fourth indexing elements may advantageously be provided with a play. This is reflected in at least one example embodiment, according to which a play (e.g. a lateral play or a radial play) between the first indexing element and the mating third indexing element is smaller than a play between said at least two second indexing element and said at least two mating fourth indexing element, whereby a tighter fit is provided between the first and third indexing elements compared to the fit between the second and fourth indexing elements.

The play between the second and fourth indexing elements makes it easy for the dentist to find the desired rotational orientation as the second indexing element will more easily be received by the fourth indexing element than what would be the case without such a play. The tight fit between the first and third indexing elements makes sure that the same rotational position is obtained throughout a multi-step procedure, e.g. making an impression with a dental component (such as a transfer coping) connected to the fixture, making a model based on the impression, making another dental component (such as an abutment) based on the model and connecting the latter dental component to the dental fixture. A potential rotational error, although small, in each step, may in the end result in a large rotational error. The tight fit between the first and third indexing elements reduces the risk of rotational errors in each step.

According to at least one example embodiment, said first and second indexing elements are provided as radial projections which project from a surface of the fixture engagement portion of the dental component, and wherein said third and fourth indexing elements are provided as radial depressions in a surface of the component engagement portion of the dental fixture. However, it would be conceivable to have it the other way around, i.e. the projections on the fixture and the depressions in the dental component. Other mixed alternatives are also conceivable as long as the second and fourth indexing elements mate before the mating of the first and third indexing elements.

According to at least one example embodiment, said at least one first indexing element is circumferentially separated from any one of said at least two second indexing elements, and wherein said at least one third indexing element is circumferentially separated from any one of said at least two fourth indexing elements.

According to at least one example embodiment, said at least two second indexing elements are asymmetrically distributed along the circumference of the fixture engagement portion, and wherein said at least two fourth indexing elements are asymmetrically distributed along the circumference of the component engagement portion.

According to at least one example embodiment, a radius from a central axis of the fixture engagement portion to the centre of one of said at least two second indexing elements and a radius from said central axis to the centre of said first indexing element form a first angle, wherein a radius from said central axis to another one of said at least two second indexing elements and said radius from said central axis to the centre of said first indexing element form a second angle, wherein said second angle is different from said first angle and from any angle being a multiple of said first angle.

According to at least one example embodiment, in the dental fixture, a radius from a central axis of the component engagement portion to the centre of one of said at least two fourth indexing elements and a radius from said central axis to the centre of said third indexing element form a first angle, wherein a radius from said central axis to another one of said at least two fourth indexing elements and said radius from said central axis to the centre of said third indexing element form a second angle, wherein said second angle is different from said first angle and from any angle being a multiple of said first angle.

According to at least one example embodiment, the dental component has at least two first indexing elements and the dental fixture has at least two mating third indexing elements. According to at least one example embodiment, the spacing between the two second indexing elements is different from the spacing between any two of said first indexing elements; and the spacing between said two fourth indexing elements is different from the spacing between any two of said third indexing elements. The two second indexing elements do not have to lie next to each other; nor do the two fourth indexing elements have to lie next to each other. There may be one or more first indexing elements which are placed between said two second indexing elements. Likewise, there may be one or more third indexing elements which are placed between said two fourth indexing elements. Also, if there are more than two second indexing elements, some of them may be spaced at the same distance as the spacing between first indexing elements, as long as there can be identified one pair of second indexing elements having a different spacing. Likewise, if there are more than two fourth indexing elements, some of them may be spaced at the same distance as the spacing between third indexing elements, as long as there can be identified one pair of fourth indexing elements having a different spacing. The advantage of this asymmetry has already been explained above in connection with the discussion of the first aspect of the invention.

According to at least one example embodiment, the fixture engagement portion and the first and second indexing elements of the dental component are rotatable inside the component engagement portion of the fixture before the second indexing elements have mated the fourth indexing elements. This facilitates the location finding function and reduces the risk of skewing of the dental component relative to the fixture. For instance, the fixture may at its coronal end have an internal socket defined by a wall portion in which third and fourth indexing elements in the form of radially extending recesses are provided. The dental component and its first and second indexing elements may be inserted into the socket and rotated. Suitably, the second indexing element, may during rotation bear upon a shelf which contains said recesses. As the dental component is rotated and the second indexing elements moves along the shelf, the second indexing elements will eventually drop into the recesses.

According to at least one example embodiment, the dental component of the dental implant according to the second aspect of the invention, is a dental component having the features discussed in connection with the first aspect of the invention.

According to a third aspect of the invention, a dental fixture adapted to be inserted into a jawbone is provided. The dental fixture comprises a component engagement portion adapted to mate with a dental component, the component engagement portion being provided with at least a first radially projecting or indenting indexing element having a coronal end, and at least two second radially projecting or indenting indexing elements, each having a coronal end which is located coronally of the coronal end of the first indexing element.

According to at least one example embodiment, the coronal end of the first indexing element is circumferentially separated from the coronal end of any one of said second indexing elements.

According to at least one example embodiment, said second indexing elements are asymmetrically distributed along the circumference of the component engagement portion.

The dental fixture according to the third aspect of the invention, may have any one of the features of dental fixtures mentioned in connection with the first and second aspects of the invention and/or any one of the features of dental fixtures mentioned in the following.

As mentioned above, a dental implant comprises a dental fixture and a dental component.

A dental fixture is for use as the anchoring member of a dental prosthesis. To this end, the dental fixture is insertable into a pre-prepared bore hole in the bone tissue of a jawbone (maxilla or mandible) at a site where the dental prosthesis is required. The dental fixture is normally rotated into the bore hole.

For screw-type dental fixtures the bore hole may be provided with internal threads in advance or may be left untapped with the dental fixture provided with a self-tapping capacity, e.g. by the provision of one or more axially-extending cutting recesses, edges or notches, etc in the fixture thread. For instance, an apical end portion of the fixture may be provided with 2-4 cutting recesses, such as 3 cutting recesses. Other number of cutting recesses are readily conceivable.

A dental component may, as discussed previously be any one of a number of different components. One example is a driver for inserting the dental fixture into the jawbone. Another example is a superstructure for connecting a prosthetic part to the fixture. The superstructure may comprise an abutment, spacer or other transmucosal component which engages to the dental fixture to bridge the gingiva overlying the maxilla or mandible. The prosthetic part, e.g. a crown, bridge or denture may be secured to the abutment. There are various other forms that the superstructure can take. For instance, the prosthetic part may be secured directly to the dental fixture.

The term "coronal" is here and throughout this application used to indicate a direction towards a head end or trailing end of the dental implant. For instance, in a situation where a dental abutment is connected to a dental fixture, the coronal direction of the abutment would be a direction towards the part of the abutment being directed away from the fixture. Conversely, the term "apical" indicates a direction towards an insertion or leading end of the component. Thus, apical and coronal are opposite directions. Furthermore, the terms "axial", "axial direction" or "axially" are used throughout this application to indicate a direction taken from the coronal end to the apical end, or vice versa. The terms "radial", "radial direction" or "radially" indicate a direction perpendicular to the axial direction.

A blind bore or socket may extend apically into the fixture body from the coronal end to an end surface in-between the apical and coronal ends of the fixture body for a superstructure to be secured to the fixture. The socket may comprise an internally-threaded section for screw connection of the dental component to the fixture. A rotational lock for the dental component may be provided in the socket, such as an internal polygonal side wall, e.g. hexagonal, or alternatively one or more protrusions from or indentation in the wall of the socket. A section of the socket, such as the coronal section, may be tapered towards the apical end. The tapered section is suitably arranged coronally of the internally-threaded section.

The fixture may be used in a one stage procedure or a two stage procedure. In a one stage procedure a healing or temporary abutment is connected to the fixture to form the gingival tissue, and after a healing period the healing or temporary abutment is replaced by a permanent abutment. For a two stage procedure the fixture is provided with a cover screw and the gingival tissue is sutured over the fixture and cover screw, and after a healing period the tissue is opened up and an abutment is connected to the fixture after removal of the cover screw.

The dental fixture may have a conically tapering end portion which tapers towards the coronal end. The axial extent of this coronal end portion is small compared to the total length of the fixture, as an example no more than 4% of the total length, such as in the range of 1.5%-3.7%. The coronal end portion may suitably be provided without a threaded surface, e.g. having a smooth or a roughened (such as blasted) surface.

The fixture may have a substantially flat coronal end surface which is perpendicular to the longitudinal axis of the fixture. Alternatively, the coronal end surface may have a sloped contour relative to the longitudinal axis of the fixture, e.g. such that when positioned within the jawbone the length of the fixture is larger on a lingual side and shorter on a buccal side of the fixture. Another alternative is a saddle-shaped or wave-like coronal end surface.

The length of the dental fixture may be in the range of 5-19 mm, depending on the clinical situation. The outer diameter of the dental fixture may suitably be in the range of 2-6 mm, such as 3-5 mm.

The fixture may be substantially cylindrical or slightly tapering from the coronal end towards the apical end. If the fixture has a slight tapering, the core of the fixture and the outer periphery defined by e.g. thread tops may have the same or different angle of taper. Furthermore, the core of the fixture may be cylindrical while the thread tops describe a conicity or, conversely, the core of the fixture may be tapered while the thread tops describe a generally cylindrical geometry. Alternatively, the fixture may comprise a combination of one or more cylindrical and/or one or more tapering portions. Thus, one or more portions of the fixture may have e.g. thread tops lying in a common imaginary cylindrical surface, which cylindrical surface is parallel with the longitudinal axis of the fixture. Alternatively or additionally, one or more portions of the fixture may have thread tops lying in an imaginary conical surface which in the apical direction is tapering towards the longitudinal axis.

The externally threaded fixture may comprise one or more thread spirals.

The term "pitch" is used to indicate the axial distance between adjacent tops of a threading. The term "lead" is used to indicate the distance advanced parallel to the longitudinal axis when the fixture is turned one revolution, i.e. it corresponds to the pitch multiplied with the number of thread spirals. For a single thread spiral having a constant pitch, the lead is equal to the pitch; for a double thread spiral, the lead is twice the pitch.

The term "microthread" is used to indicate a thread having a height which is no greater than 0.2 mm. According to at least one example embodiment, the fixture is provided with microthreads having a height in the range of 0.02-0.2 mm, such as 0.05-0.015 mm, for instance 0.1 mm. The term "macrothread" is used to indicate a thread having a height which is greater than 0.2 mm. According to at least one example embodiment, the fixture is provided with macrothreads having a height in the range of 0.25-0.35 mm, such as 0.3 mm.

Suitably, microthreads may be located coronally of macrothreads. For instance, microthreads may be arranged to engage dense cortical bone and macrothreads may be arranged to engage porous spongious/cancellous bone. The lead of a microthread suitably corresponds to the lead of a macrothread. The macrothread pitch may, as an example, be 2-4 times, such as 3 times, the pitch of the microthreads. The pitch (top-to-top spacing) at a fixture portion provided with microthreads may be around 0.10-0.30 mm, for instance 0.20-0.24 mm. The pitch (top-to-top spacing) at a fixture portion provided with macrothreads may be around 0.30-0.90 mm, for instance 0.60-0.72 mm.

Microthreads can be regarded as defined, oriented roughness. A non-oriented roughness having smaller dimensions, for instance obtained by blasting, etching, etc., may be superimposed on microthreads as well as on macrothreads.

A thread profile may comprise two flanks, a top interconnecting said two flanks, a bottom formed between two adjacent threads, said flanks forming an acute angle v with a plane which is perpendicular to the fixture axis and which angle v lies in a plane containing the extension of the fixture axis, said profile further having a height D. The top may be curved and may have a top radius. Suitably, for $10°≤v<35°$, the top radius is greater than $0.4×D$ and, for $35°≤v<55°$, the top radius is greater than $0.2×D$.

BRIEF DESCRIPTION OF THE DRAWINGS

FIG. 2 illustrates a dental component according to at least one other example embodiment of the invention, which is to be connected to a dental fixture in a specific rotational orientation with respect to the dental fixture, wherein the dental component and the dental fixture together represent a dental implant according to at least one example embodiment of the invention. FIG. 2 also illustrates another dental component which may be arranged in a number of different rotational orientations with respect to the same dental fixture.

DETAILED DESCRIPTION OF THE DRAWINGS

Each drawing illustrates a dental component having first and second indexing elements, and some of the drawings also illustrate a dental fixture having third and fourth indexing elements.

Figure 1A:
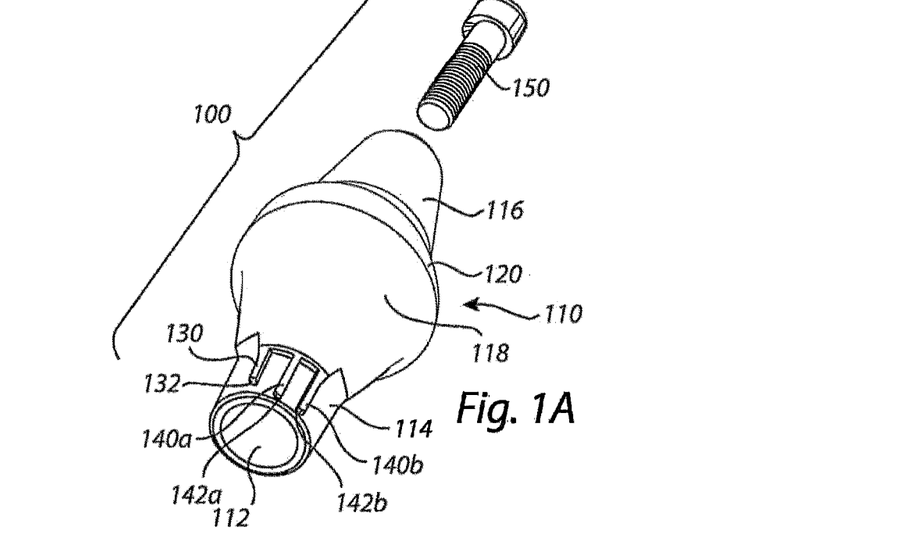
FIGS. 1A-1C illustrate a dental component according to at least one example embodiment of the invention.
Figure 1B:
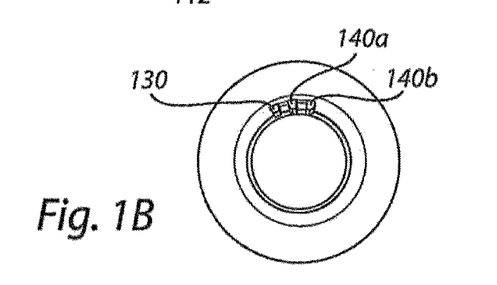
Figure 1C:
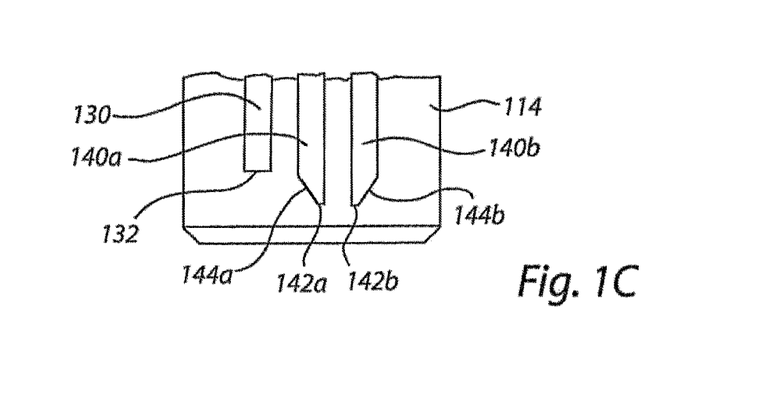

FIGS. 1A-1C illustrate a dental component 100 according to at least one example embodiment of the invention, wherein FIG. 1A is a perspective view, FIG. 1B is a bottom view and FIG. 1C is a partial side view. The dental component 100 may, for instance, be an abutment, an abutment replica or an abutment blank. The dental component 100 comprises a body part 110 which is provided with a central through-hole 112, through which a screw part 150 is insertable and connectible to internal threads of a dental fixture, in order to secure the body part 110 to the fixture. The body part 110 comprises a fixture engagement portion 114, which is herein illustrated as having a generally cylindrical enveloping surface, although other enveloping surfaces, such as tapering, would be a conceivable alternatives. The body part 110 further comprises a dental crown-receiving or prosthesis-receiving portion 116 which extends coronally of the fixture above the gingiva. An extension portion 118, herein illustrated as coronally flaring up to a shoulder 120, is intended to extend through the gingiva and is provided between the fixture engagement portion 114 and the prosthesis-receiving portion 116. In case the dental component 100 is provided as an abutment blank, at least one of the extension portion 118 and the prosthesis-receiving portion 116 may be further processed to a desired shape, which may suitably be customized for the patient receiving the resulting processed abutment.

The fixture engagement portion 114 is provided with a radially projecting first indexing element 130 having an apical end 132, and two radially projecting second indexing elements 140a, 140b having apical ends 142a, 142b. The apical ends 142a, 142b of the second indexing elements 140a, 140b are located apically of the apical end 132 of the first indexing element 130. The overall axial extension of the first indexing element 130 and the second indexing elements 140a, 140b is such that the first indexing element 130 and the second indexing elements 140a, 140b are intersected by a common geometrical plane which is perpendicular to the central axis of the fixture engagement portion 114. Thus, the axial extension of the first indexing element 130 is at least partly overlapped by the axial extension of the second indexing elements 140a, 140b.

Following the circumference of the fixture engagement portion 114, the first indexing element 130 is located at a position which is spaced from the positions of the second indexing elements 140a, 140b, i.e. the first indexing element 130 is circumferentially separated from any one of the second indexing elements 140a, 140b. Expressed differently, in a cylindrical coordinate system (r, $\phi$, z) wherein the z axis coincides with the central geometrical axis of the engagement portion 114, the angle $\phi$ will be different for each one of the first indexing element 130 and the two second indexing elements 140a, 140b.

The close positioning of the two second indexing elements 140a, 140b results in that they are asymmetrically distributed along the circumference of the fixture engagement portion 114. Asymmetrical distribution means that the two second indexing elements are not evenly distributed around the fixture engagement portion. An even, symmetrical distribution would have the two second indexing elements distributed 180° from each other around the fixture engagement portion 114.

This dental component 100 may be connected to a dental fixture having indexing elements in the form of indexing indentations/recesses/depressions which sizewise match the indexing elements 130, 140a, 140b of the dental component 100. Thus, as the dental component 100 is brought into contact with the fixture, the second indexing elements 140a, 140b will be leading and will be the first to enter associated indexing recesses in the fixture. Once the second indexing elements 140a, 140b have mated with their associated indexing recesses in the fixture, the trailing first indexing element 130 of the dental component 100 will be substantially aligned with its associated indexing recess. Therefore, when the dental component 100 is continued to be inserted into the fixture, the first indexing element will easily mate with its associated indexing recess in the fixture. Thus, the leading second indexing elements 140a, 140b have an initial guiding/aligning function while the trailing first indexing element 130 completes the rotational locking.

In FIGS. 1A-1C the indexing elements 130, 140a, 140b have been confined to a small area of the fixture engagement portion 114. This small area spans over approximately 60° of the total (360°) circumference of the fixture engagement portion 114, the central (second) indexing element 140a being spaced from its neighbours at approximately 30°. The dental component 100 may thus mate with a fixture having similar distribution of indexing elements, one exemplary fixture 4 being illustrated in FIG. 2. The three indexing elements or indexing recesses of the fixture 4 in FIG. 2 which would mate the indexing elements 130, 140a, 140b of the dental component 100 in FIG. 1 are denoted 30e, 30f, 30g. The fixture 4 has four other indexing elements 30a-30d, however, these are separated at a larger distance. Thus, the dental component 100 can only mate with this fixture 4 in one rotational orientation. If one of the second indexing elements (e.g. 140a), would be aligned over an incorrect indexing element in the fixture 4, the other second indexing element (e.g. 140b) will rest against a shelf 32 in the fixture 4, thus rendering further apical movement difficult. If there would have been only one second indexing element, it could have dropped into any one of the seven indexing recesses 30a-30g in the fixture 4, before the dentist realizes that the dental component is incorrectly orientated. Although, having two second indexing elements stabilizes and reduces the risk of one of the second indexing elements 140a, 140b dropping into an undesired indexing recess of the fixture, it may accidently happen if e.g. the dentist tilts the dental component too much. Therefore, turning back to FIG. 1C, as an optional feature the second indexing elements may be provided with a respective chamfer 144a, 144b, on the side facing away from the other second indexing element. Such a chamfer 144a, 144b facilitates continued rotating movement by the dentist in case one of the second indexing elements 140a, 140b would slightly drop into an incorrect indexing recess. As a further optional feature, the second indexing elements 140a, 140b may have a somewhat smaller radial or circumferential extension compared to the first indexing element 130, in order to provide a certain play when mating with the indexing recesses of the fixture 4. In such case, even though the second indexing elements 140a, 140b may not provide a sufficient rotational lock, their underdimensioning will facilitate the location finding function, and the first indexing element 130 can still be relied upon for the rotational locking function.

It should be noted that the dental component 100 is not limited to be used with fixtures permitting only one rotational orientation. The dental component 100 could for instance be connected to a fixture having twelve indexing recesses, each recess being equidistantly spaced at 30° from the neighbouring recesses. With such a fixture, the dentist may select any one of twelve rotational positions for the dental component 100. Thus, the exemplified dental component 100 maintains the possibility of multiple rotational positioning with some types of fixtures, while providing the above-presented benefits in connection with fixtures permitting only a single rotational positioning.

FIG. 2 illustrates a dental component 2 according to at least one other example embodiment of the invention, which is to be connected to a dental fixture 4 in a specific rotational orientation with respect to the dental fixture 4, wherein the dental component 2 and the dental fixture 4 together represent a dental implant according to at least one example embodiment of the invention. FIG. 2 also illustrates another dental component 6 which may be arranged in a number of different rotational orientations with respect to the same dental fixture 4.

The herein illustrated dental fixture 4 has a coronal portion 8 extending apically from a coronal end 12 of the fixture 4, and an apical portion 10 extending coronally from an apical end 14 of the fixture 4.

The apical portion 10 may have a conicity tapering towards the apical end 14 of the fixture 4 to ease insertion of the fixture 4 into a bore-hole in the jawbone.

The fixture 4 has a core from which a surface structure projects, in the illustrated example being in the form of threads.

The coronal portion 8 is herein illustrated as being at least partly provided with microthreads 16, e.g. having three thread spirals, although another number is conceivable, such as 1, 2, 4 or more spirals. Although microthreads 16 have been illustrated, according to at least an alternative example embodiment the coronal portion 8 is at least partly provided with macrothreads 18, similarly to the apical portion 10, either as a separate thread spiral or as a continuation of the thread spiral at the apical portion 10. According to at least another alternative example embodiment, instead of microthreads 16, the coronal portion may be provided with a plurality of annular ridges, which to the naked eye could give the same visual appearance as microthreads. Other conceivable alternatives are circumferential lines of beads or non-oriented/randomly provided projections such as bulges.

In the illustrated example embodiment, the macrothreads 18 at the apical portion 10 has the same lead as the microthreads 16 at the coronal portion 8. However, the pitch of the macrothreads 18 is three times the pitch of the microthreads 16, since the microthreads 16 comprise three thread spirals.

The apical portion 10 comprising macrothreads 18 is herein illustrated as having one thread spiral, however, the apical portion 10 may alternatively have two or more thread spirals.

The length of the herein illustrated coronal portion 8 may be about 1-2 mm, such as 1.5 mm. However, shorter or longer lengths are readily conceivable. The relative length of the coronal portion 8 may also be selected from a wide range, such as 5-50% of the total length of the fixture 4, e.g. 10-20%.

The coronal portion 8 comprises a tapering end portion 20, which tapers towards the coronal end 12 of the fixture 4. The tapering end portion 20 is no more than 4% of the total length of the fixture 4. The surface of the tapering end portion 20 may be non-threaded, either smooth or blasted (or otherwise roughened).

Cutting recesses 22 or grooves extend coronally from the apical end 14. The number of cutting recesses 22 may be one or more, such as two, three or four cutting recesses, suitably symmetrically positioned about the circumference of the apical end 14 of the fixture 4 for self-tapping of the fixture 4 when being screwed/rotated into the bore-hole provided in the maxilla or mandible.

A socket 24 having an open end is provided in the coronal end 12 of the fixture 4. The socket 24 extends apically into the fixture 4. The socket 24 is for receiving a dental component 2 such as the illustrated abutment which will bridge the gingiva overlying the bore-hole and support/present a prosthetic part. However, it may also receive other dental components such as an abutment replica, a driver, a healing cap, an impression pick-up element, a digital transfer coping, etc.

Figures 2A, 2B, 2C:
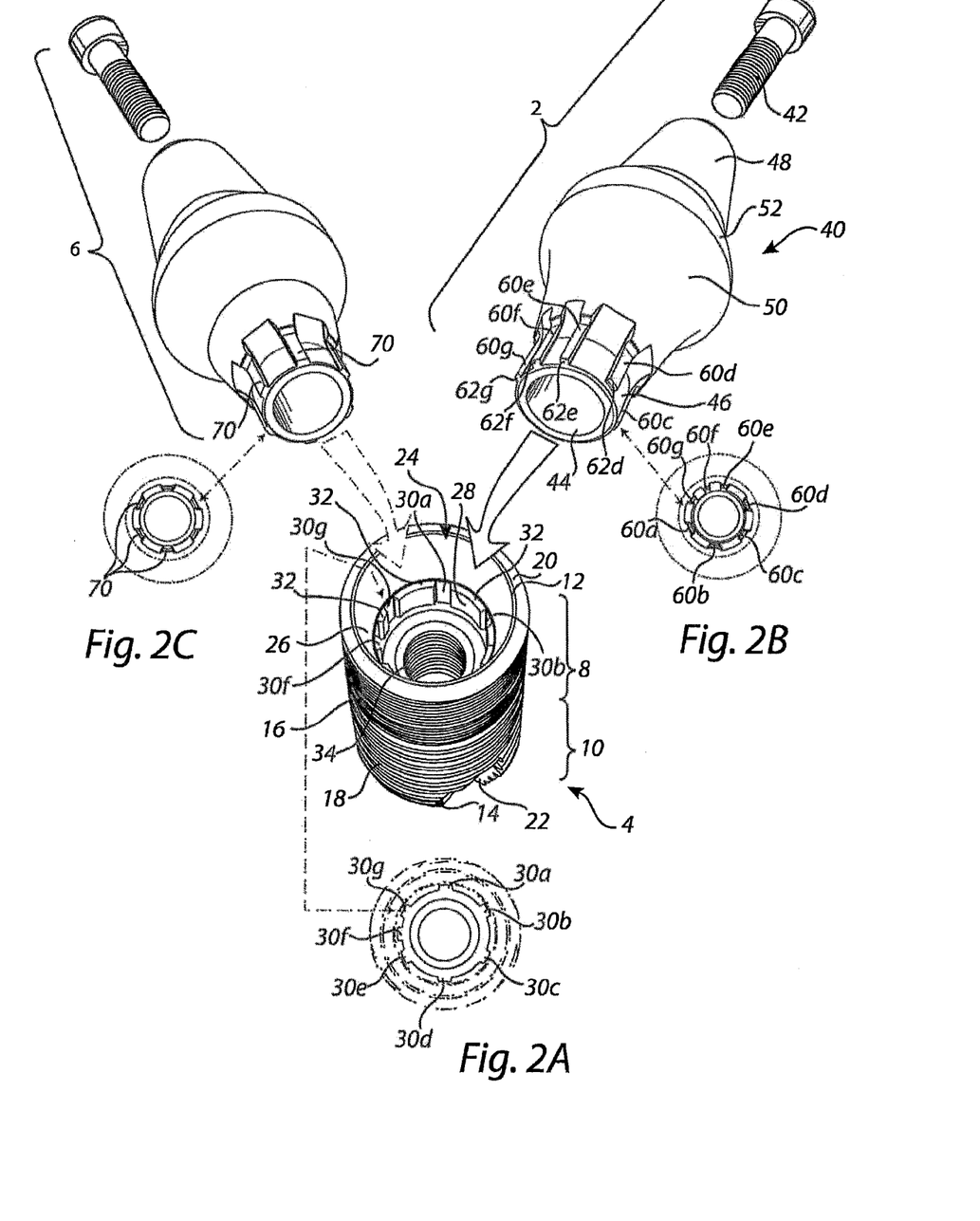
FIG. 2A is a top view of the dental fixture in FIG. 2.
FIGS. 2B-2C are bottom views of the dental components in FIG. 2.

Although various alternative configurations are conceivable, the socket 24 is herein illustrated as having a conical coronal section 26 and a substantially cylindrical intermediate wall section 28. Seven indexing elements 30a-30g, herein illustrated as radially extending recesses 30a-30g are provided in the intermediate wall section 28 (see also FIG. 2A). The intermediate wall section 28 and the radially extending recesses 30a-30g act as a component engagement portion of the fixture 4. The coronal end of the intermediate wall section 28 forms a shelf 32 with gaps formed by said seven recesses 30a-30g. Six of the recesses 30a-30e, 30g are equidistantly distributed along the circumference of the intermediate wall section 28. The seventh recess 30f is interposed between two (30e, 30g) of said six equidistantly distributed recesses. This is clearly illustrated in the top view of FIG. 2A.

The socket 24 is further provided with an internally threaded apical section 34.

A dental component 2 according to at least one example embodiment of the invention is herein illustrated as a two-piece abutment 2 consisting of a body part 40 and a screw part 42. The body part 40 of the abutment 2 is provided with a through-hole 44, wherein the screw part 42 is adapted to be inserted into the through-hole 44 and engage the internal thread 34 of the fixture 4 in order to secure the body part 40 to the fixture 4. The body part 40 comprises a fixture engagement portion 46, which is herein illustrated as having a generally cylindrical enveloping surface, although other enveloping surfaces, such as tapering, would be a conceivable alternatives. The body part 40 further comprises a dental crown-receiving or prosthesis-receiving portion 48 which extends coronally of the fixture 4 above the gingiva. An extension portion 50, herein illustrated as coronally flaring up to a shoulder 52, is intended to extend through the gingiva and is provided between the fixture engagement portion 46 and the prosthesis-receiving portion 48.

Seven indexing elements 60a-60g, herein illustrated as radial projections 60a-60g, are provided sequentially in the circumferential direction of the cylindrical enveloping surface of the fixture engagement portion 46 (see also 2B). Similarly to the distribution of the radial recesses 30a-30g in the fixture 4, there are six equidistantly distributed radial projections 60a-60e, 60g on the dental component 2, while the seventh radial projection 60f is interposed between two (60e, 60g) of said six equidistantly distributed radial projections. With this configuration, the seventh radial projection 60f and its two neighbouring radial projections 60e, 60g can only mate in one correct way with the seventh radial recess 30f and its two neighbouring recesses 30e, 30g. Thus, there is only one rotational orientation possible for the dental component 2 to be connected with respect to the dental fixture 4.

Four of the radial projections can be regarded as first indexing elements 60a-60d, each having an apical end (in FIG. 2 the apical end of the indexing element 60d is designated with reference numeral 62d). The other three radial projections 60e-60g, namely said seventh radial projection 60f and its two neighbouring projections 60e, 60g, can be regarded as second indexing elements 60e-60g having apical ends 62e-62g located apically of the apical ends of the first indexing elements 60a-60d. This facilitates for the dentist to connect the dental component 2 to the dental fixture 4 in the correct rotational orientation. Contrary to the example embodiment shown in FIG. 1, in this example embodiment the number of first indexing elements 60a-60d is greater than the number of second indexing elements 60e-60g. In the circumferential direction of the fixture engagement portion 46, each one of the first indexing elements 60a-60d is located at a position which is different from the positions of the second indexing elements 60e-60g. Thus, each one of the first indexing elements 60a-60d is circumferentially separated from any one of the second indexing elements 60e-60g.

When the body part 40 of the abutment 2 is to be connected to the fixture 4, the projections forming said second indexing elements 60e-60g may come in contact with the shelf 32 in the fixture 4. The projections forming said first indexing elements 60a-60d will still be spaced from the shelf 32. The body part 40 is then rotated so that the second indexing elements 60e-60g fall into the designated recesses 30e-30g of the fixture 4, i.e. into the seventh recess 30f and its two neighbouring recesses 30e, 30g.

Thus, the second indexing elements 60e-60g will first engage with the seventh recess 30f and its two neighbouring recesses 30e, 30g which represent fourth indexing elements 30e-30g, and thereafter having already found the correct rotational position, the first indexing elements 60a-60d of the dental component 2 can engage with the third indexing elements 30a-30d (the other four recesses 30a-30d) of the dental fixture 4.

If only a single one (for example 60f) of the seven indexing elements 60a-60g of the dental component 2 would have an apical end located apically of the other six indexing elements, that single one (for example 60f) of the indexing elements 60a-60g could have mated with any one of the seven indexing elements 30a-30g of the fixture 4. However, only one (in this example 30f) of those seven indexing elements 30a-30g of the fixture is the correct one which allows the trailing indexing elements of the dental component to also mate with the corresponding indexing elements in the fixture. If the dentist would place said single one (e.g. 60f) of the seven radially projecting indexing elements 60a-60g into one of the six incorrect radially indented indexing elements (e.g. 30a-30e, 30g), the trailing indexing elements (e.g. 60a-60e, 60g) of the dental component 2 would not find a mating indexing element in the fixture 4 but would abut the shelf 32. The dentist would have to lift the dental component 2 and try again to find the correct rotational orientation of the dental component 2 relative to the fixture 4. By additionally letting another one (for example 60g) of the seven indexing elements (60a-60g) have an apical end extending apically of the apical ends of the other indexing elements, said indexing element (in this example 60g) will be in contact with the shelf 32 of the fixture reducing the risk of the other indexing element (in this example 60f) falling into the incorrect recess in the fixture 4. Thus, having a dental component with at least one first indexing element and at least two second indexing elements having apical ends apically of the apical end of the first indexing element reduces the risk of the second indexing elements falling into the incorrect recesses in the fixture. Nevertheless, if the dentist brings the dental component 2 towards the fixture 4 in a slightly inclined direction, one of said second indexing elements may still be able to reach into an incorrect recess in the fixture, albeit not very deeply because of the other second indexing element contacting the shelf 32 preventing further advancement. Because the second indexing element cannot fall deeply into an incorrect recess, a rotating motion will easily lift the second indexing element and after continued rotation the correct position will be found.

Figure 3:
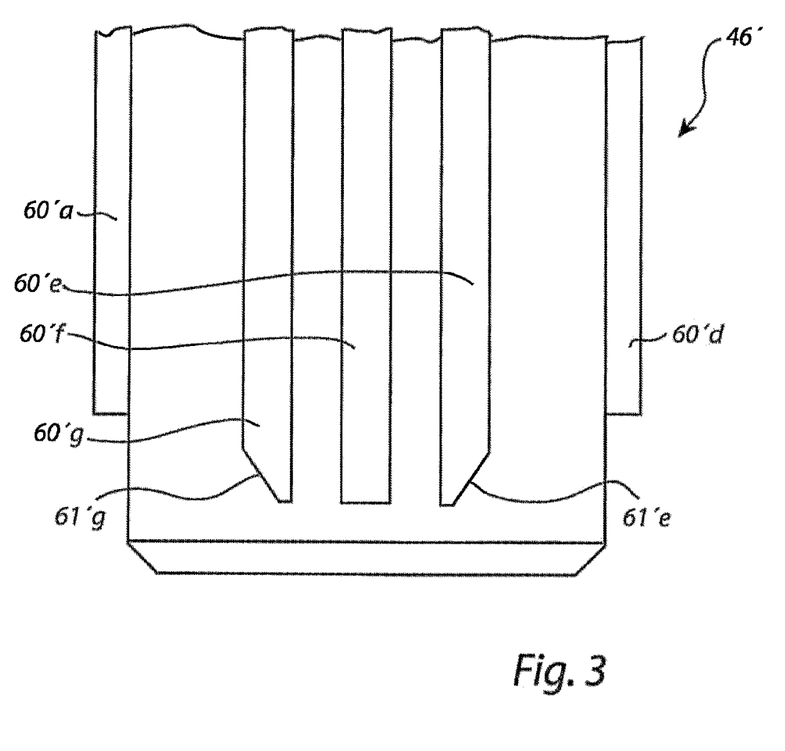
FIG. 3 illustrates a fixture engagement portion of a dental component according to at least one example embodiment.

Having three radially projecting second indexing elements with longer apical extensions than the trailing first indexing element further facilitates correct alignment of the indexing elements of the dental component with those of the fixture. FIG. 2 illustrates an advantageous distribution of three second indexing elements 60e-60g interposed between two (60a, 60d) of the first indexing elements 60a-60d. The middle one (60f) of the second indexing elements 60e-60g cannot fall into an incorrect recess (30a-30e, 30g) in the fixture 4, because of the other two (60e, 60g) second indexing elements provided on either side thereof. When the dental component 4 is to be connected to the fixture 2, the second indexing elements 60e-60g will with high likelihood land on the shelf 32, thus requiring the dentist to rotate the dental component 4 into the correct orientation. During such rotation, unless the dentist holds the dental component 4 absolutely straight, one of the two outer second indexing elements (60e, 60g) might just slightly drop into an incorrect recess in the fixture. Since the drop is so small, the dentist can easily continue the rotation until the correct alignment is found. Nevertheless, in FIG. 3, showing a fixture engagement portion 46' of a dental component, an example embodiment is illustrated in which each one of the two outer second indexing elements 60'e, 60'g are provided with a respective chamfer 61'e, 61'g on the side facing away from the middle one (60'f) of the second indexing element. Such a chamfer 61'e, 61'g further facilitates the continued rotating movement by the dentist in case one of the outer second indexing elements 60'e, 60'g would slightly drop into an incorrect recess. In FIG. 3, two shorter first indexing elements 60'a, 60'd are also visible. Also, it may be noted that the apical ends of the second indexing elements 60'e-60'g are not flush with the apical end of the dental component as in FIG. 2, but instead located somewhat coronally thereof.

As illustrated in the bottom view of FIG. 2B, the first indexing elements 60a-60d are somewhat wider than the second indexing elements 60e-60g. In the dental fixture 4, however, the third and fourth indexing elements 30a-30g have substantially the same width. This has the effect that due to a larger width difference between the second indexing elements 60e-60g and the fourth indexing elements 30e-30g, there will be a lateral play between these indexing elements facilitating the finding of the correct rotational orientation. In other words, because the radially projecting second indexing elements 60e-60g are laterally/transversely underdimensioned with respect to the radially indenting fourth indexing elements 30e-30g, they will more easily fall into place than if they were of substantially the same dimensions. The radially projecting first indexing elements 60a-60d are dimensionally closer matched to the radially indenting third indexing elements 30a-30d, reducing potential lateral play, and instead ensuring a substantially well-defined rotational position of the dental component 2 with respect to the dental fixture 4. It should be understood that rather than making the second indexing elements 60e-60g narrower than the first indexing elements 60a-60d, an option would be to make them of equal width and instead make the fourth indexing elements 30e-30g wider than the third indexing elements 30a-30d. Thus, the relatively large lateral play between the second and fourth indexing elements can be accomplished with various designs of the dental component and/or dental fixture.

In FIG. 2, the second indexing elements 60e-60g have been illustrated as extending all the way to the apical end of the body part 40, however, other alternatives are conceivable. For instance, the second indexing elements 60e-60g may extend somewhat shorter, as long as the apical ends 62e-62g thereof are located apically of the apical ends of the first indexing elements 60a-60d, or they may extend longer, i.e. beyond the apical end of the body part (see e.g. FIG. 3). FIG. 3 additionally shows one of a plurality of portions of the cylindrical enveloping surface of the fixture engagement portion 114, extending between two first indexing elements 60' a and 60' d and containing the second indexing elements 60' e-g.

Furthermore, it should be noted that the coronal extension of the second indexing elements 60e-60g may also be shorter. In fact, it should be understood that, for the radially projecting second indexing elements 60e-60g to fall into connection with the radially indenting fourth indexing elements 30e-30g, the second indexing elements 60e-60g could be designed as substantially flat plates projecting from the surface of the fixture engagement portion 46 of the body part 40. Once the flat plates are received by the associated recesses 30e-30g, the whole body part 40, including the following indexing elements 60a-60d (i.e. the other radial projections which have the purpose to provide a rotational lock) will be guided in the desired direction for completing the insertion of the body part 40 into the dental fixture 4.

It should also be noted that, although second indexing elements 60e-60g have been presented in FIG. 2 as the seventh radial projection 60f and its two neighbouring radial projections 60e, 60g, other alternatives are possible. For instance, the seventh radial projection 60f and a non-neighbouring projection (such as projection 60a, 60b or 60c) could have their apical ends located apically of the apical ends of the other radial projections. These two radial projection would be leading and be the first ones to abut the shelf 32 provided between the recesses in the dental fixture 4. They can only fall down from the shelf when the seventh radial projection 60f is aligned with the seventh radial recess 30f. Thus, in general terms, according to at least one example embodiment, the distribution of the second indexing elements around the fixture engagement portion is asymmetrical relative to the distribution of the first indexing elements. In other words there is at least one pair of second indexing elements (for instance corresponding to the illustrated positions of 60f/60g, or 60f/60a, or 60f/60b) spaced differently than the spacing between any pair of first indexing elements.

FIG. 2 and FIG. 2C also illustrate another dental component 6 in the form of an abutment 6. It has six equally-dimensioned and equidistantly distributed indexing elements in the form of radial projections 70. Unlike the first abutment 2, this other abutment 6 lacks a seventh projection. Thus, this other abutment 6 may be connected to the dental fixture 4 in six different rotational orientations.

FIGS. 4A-4E illustrate schematically circumferential distributions of first and second indexing elements on dental components according to different example embodiments. Although not viewable from the drawings, in each of these example embodiments each one of the second indexing elements has an apical end located apically of the apical ends of the first indexing elements.

Figure 4A:
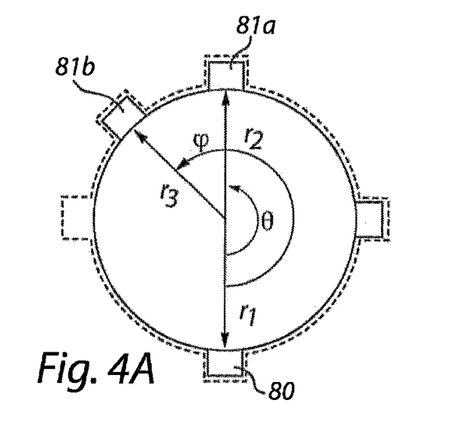
FIGS. 4A-4E illustrate schematically circumferential distributions of first and second indexing elements on dental components according to different example embodiments.

In FIG. 4A, the dental component is provided with one first indexing element 80 and two second indexing elements 81a, 81b. A radius $r_1$ from the central axis to the centre of said first indexing element 80 and a radius $r_2$ from the central axis to the centre of one 81a of the second indexing elements form a first angle $\theta$. A radius $r_3$ from the central axis to the centre of the other one 81b of said second indexing elements and said radius $r_1$ from the central axis to the first indexing element 80 form a second angle $\phi$. The second angle $\phi$ is different from said first angle $\theta$ and any angle being a multiple of said first angle $\theta$. In other words, $\phi \neq n\theta$, where n is a positive integer. The dashed line illustrate the contour of receiving indexing elements in the fixture. As can be seen not all of the indexing elements in the fixture are occupied by indexing elements of the dental component. Because of the asymmetry, the dental component can only mate in one correct rotational orientation with the fixture.

In connection with FIG. 4A, the following should be noted. The angle $\theta$ defining the positions of the first indexing element 80 and one 81a of the second indexing elements is illustrated as being 180°. Assuming a dental component would be manufactured differently, with the position of the first indexing element 80 and the position of the other one 81b of the second indexing elements being switched, then the two second indexing elements would have been located at 180° with respect to each other. If a dentist misplaces the dental component by 90°, the two oppositely located second indexing elements could enter receiving indexing elements in the fixture. However, the first indexing element would land on a shelf. When the dentist wishes to rotate the dental component to the correct position, he/she will experience a non-smooth, intermittent motion. However, the illustrated configuration in FIG. 4A, with the second indexing elements 81a, 81b being asymmetrically arranged will make the location finding process much smoother. Even if one of the second indexing elements would catch into an incorrect indexing element in the fixture, the other second indexing element will prevent it from falling too deeply, since both of the second indexing elements 81a, 81b have an apical end located apically of the apical end of the first indexing element 80.

Figure 4B:
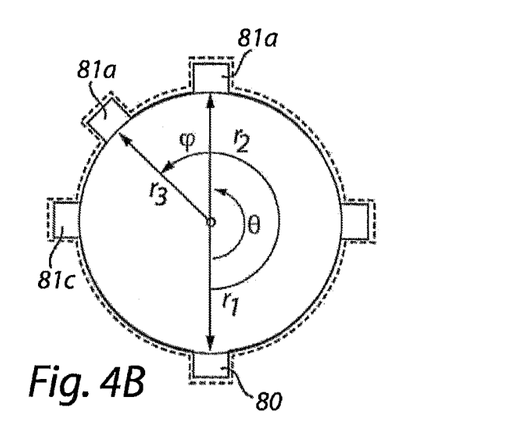

In the embodiment of FIG. 4B, an additional second indexing element 81c is provided, compared to the embodiment in FIG. 4A. The three indexing elements 81a-81c makes the location finding even smoother.

Figure 4C:
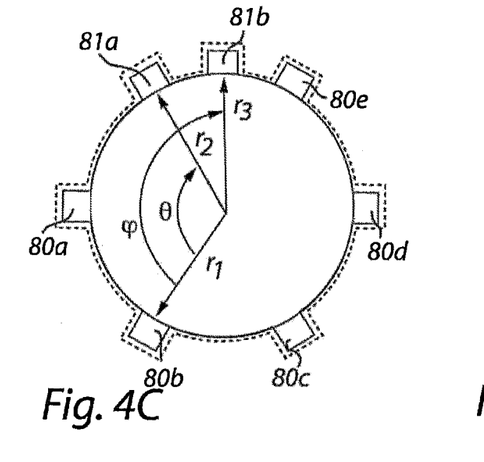

In the embodiment of FIG. 4C, the dental component is provided with five first indexing elements 80a-80e and two second indexing elements 81a, 81b. The five first indexing elements 80a-80e and one 81a of the second indexing elements are equidistantly arranged at 60° intervals. The other one 81b of the second indexing elements is interposed and spaced at 30° from its neighbouring indexing elements 80e, 81a. The previously described first angle will, depending on which one of the first indexing elements 80a-80e is selected as a reference point, have a value of n*60° in relation to one 81a of second indexing elements, where n=1, 2, 3, 4, 5. In FIG. 4C the first indexing element 80b has been chosen (n=2), wherein the first angle $\theta=120°$ and the second angle $\phi=150°$.

Figure 4D:
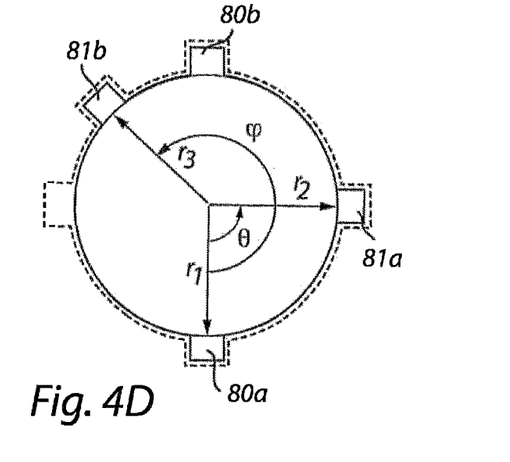

In the embodiment of FIG. 4D, the dental component is provided with two first indexing elements 80a, 80b and two second indexing elements 81a, 81b. Unlike in the previous illustrations, the two second indexing elements 81a, 81b are not neighboring to each other in FIG. 4D. The first angle θ=90° and the second angle φ=225°. Thus, the relationship φ≠nθ is valid also for this example embodiment.

Figure 4E:
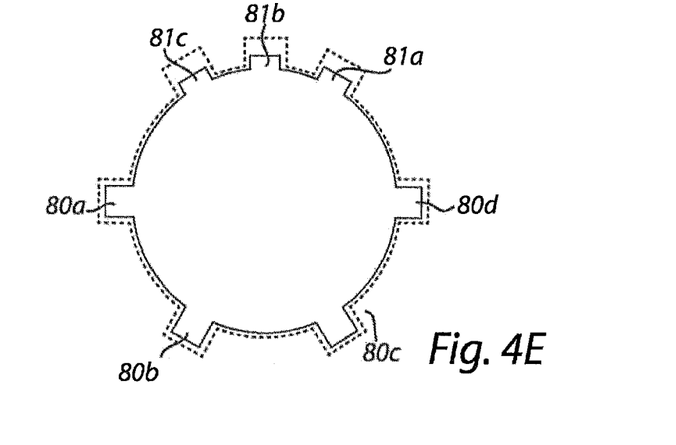

In FIG. 4E the distribution corresponds to that in FIG. 2, thus four first indexing elements 80a-80d and three second indexing elements 81a-81c. It is also similar to the distribution in FIG. 4C, with the exception that one of the first indexing elements has now been replaced by a second indexing element. The second indexing elements 81a-81c have a smaller dimension in the radial direction than the first indexing elements 80a-80d. Thus, when placed in a fixture having substantially uniformly recessed indexing elements, there will be a larger play in the radial direction between the second indexing elements 81a-81c and the walls of the mating indexing element in the fixture than any play in the radial direction between the first indexing elements 80a-80d and the walls of their mating indexing elements. Once the correct rotational position is found, the larger play facilitates insertion of the second indexing elements 81a-81c into the mating recessed indexing elements of the fixture.

Figure 5:
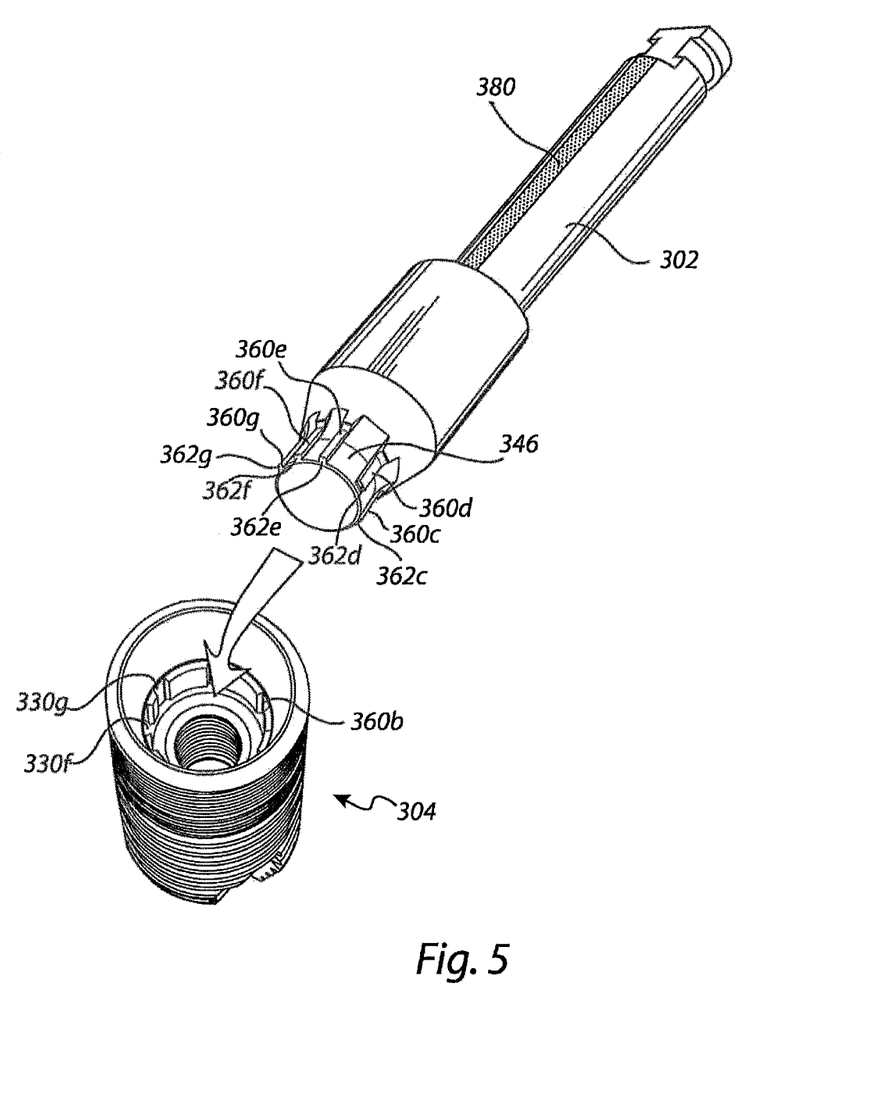
FIG. 5 illustrates, in accordance with at least one example embodiment, a dental component in the form of a driver to be connected to a dental fixture.

FIG. 5 illustrates, in accordance with at least one example embodiment, a dental component in the form of a driver 302 to be connected to a dental fixture 304. In this example, the interface between the dental fixture 304 and the driver 302 corresponds to the interface between the dental fixture 4 and dental component 2 illustrated in FIG. 2. Thus, the driver 304 has three radial projections (second indexing elements 360e-360g) having an apical end 362e-362g located apically of the apical ends (only 362c, 362d shown) of the other four radial projections (first indexing elements 360c, 360d; only two out of four can be seen in the perspective view shown in FIG. 5). The fixture has mating third and fourth indexing elements, respectively (only one third indexing element 330b and two fourth indexing elements 330f and 330g can be seen in this view). Thus, similarly to the connection in FIG. 2, the driver 302 can only be connected in one rotational orientation relative to the fixture 304.

The driver 302 is used for rotatingly driving the fixture 304 into a bore hole in the jawbone. The driver may be designed as a piece which can be used on its own, or alternatively, at its coronal end, the driver may be designed to be connectible to a handle, a wrench (such as a ratchet wrench), a power driver machine, etc.

The driver 302 is provided with a visually distinctive marking 380, herein illustrated as an axial line, aligned with the middle second indexing element 360f at the fixture engagement portion 346 of the driver 302. The distinctive marking 380 may have a color which is different from the rest of the driver 302, it may have different texture, or be slightly bulging, or any other appropriate viewable distinction compared to the rest of the driver.

The driver 302 can only be positioned in a single rotational indexing position relative to the fixture 304, meaning that each time the driver 302 engages such a fixture 304, the rotational position of the distinctive marking 380 relative to the fixture 304 will always be the same. Thus, by viewing the axial line provided by the marking 380, a user will be able to deduce the rotational position of the fixture 304 in the jawbone. This allows pre-planning and designing of the surgical and laboratory procedure before a dental fixture 304 is even inserted into the bone. For instance, a scan of the tooth-less site can be made, and a complete patient-specific implant may be designed in which the abutment should have a certain orientation relative to the fixture 304 and relative to the surrounding tissue, and therefore the fixture 304 should have a certain orientation in the jawbone.

A driver, such as the driver 302 illustrated in FIG. 5, may suitably be used with other dental fixtures. According to at least one example embodiment, the driver adapted to be connected to a dental fixture having a coronal end portion which is not flat. For instance, the fixture may have a sloped coronal end portion, in which the length of the fixture is greater on the lingual side than on the buccal side in order to match the contour of the jawbone. During installation of the fixture in the jawbone, the distinctive marking of the driver will indicate to the dentist in which direction the coronal end portion of the fixture is sloping, thus allowing the dentist to make appropriate adjustments to correctly align the slope of the fixture with the slope of the jawbone.

Although the drawings have illustrated dental components provided with indexing elements in the form of radial projections and dental fixtures with indexing elements in the form of radial recesses, it should be understood that in other embodiments, the indexing elements of the dental components may instead be radial recesses and the indexing elements of the fixtures may be radial projections.

Furthermore, although the drawings have illustrated that the dental component as a male component having a fixture engagement portion to be inserted into a socket of the fixture (acting as a female component), other embodiments are also conceivable. For instance, the fixture may have a summit portion, which may suitably be adapted to extend beyond the bone crest, and apical end of the dental component may be provided with an socket extending coronally into the dental component, whereby the socket is intended to be placed onto the summit portion. Radially projecting or indenting indexing elements may be provided also for such a component/fixture interface.

Although the indexing elements have been illustrated as elongate radial projections and recesses, in other embodiments they would not be elongate. Furthermore, the cross-section of the indexing elements may be of any suitable shape, such as curved, triangular, rectangular, trapezoid, or any other regular or irregular shape.

It should also be noted that the number of indexing elements in the dental component does not necessarily have to be equal to the number of indexing elements in the dental fixture. For instance, in FIG. 2, one of the radial projections forming a first indexing element could be removed, although the effect of the rotational lock will be somewhat weakened.

The invention claimed is:

1. A dental implant, comprising a dental component and a dental fixture, the dental component including:
   a fixture engagement portion provided with
      at least two radially projecting first indexing elements, each having an apical end, the at least two radially projecting first indexing elements include a primary first indexing element and a secondary first indexing element being spaced from one another by a first cylindrical enveloping surface portion therebetween; and
      at least two radially projecting second indexing elements being circumferentially spaced from one another and interposed circumferentially in the first cylindrical enveloping surface portion and between the primary first indexing element and the secondary first indexing element, wherein the first cylindrical enveloping surface portion is free of additional radially protecting first indexing elements;

the dental fixture adapted to be inserted into a jawbone and comprising
- a component engagement portion adapted to mate with said fixture engagement portion, the component engagement portion being provided with at least two third indexing elements having a coronal end, and at least two fourth indexing elements being adjacent to one another, each one having a coronal end, wherein at least one of the apical ends of said at least two second indexing elements are located further apically relative to the apical ends of the at least two first indexing elements and/or the coronal ends of said at least two fourth indexing elements are located further coronally relative to the coronal ends of the at least two third indexing elements, wherein the first and second indexing elements are radially spaced from one another and are distributed along the circumference of the fixture engagement portion and the third and fourth indexing elements are radially spaced from one another and are distributed along the circumference of the component engagement portion, respectively, in such way that the dental component can only mate in one rotational orientation with respect to the dental fixture, and wherein the two first indexing elements are only enabled to mate with the two third indexing elements after said at least two second indexing elements have mated with said at least two fourth indexing elements.

2. The dental implant as claimed in claim 1, wherein a play between the first indexing elements and the mating third indexing elements is smaller than a play between said at least two second indexing elements and said at least two mating fourth indexing elements, whereby a tighter fit is provided between the first and third indexing elements compared to the fit between the second and fourth indexing elements.

3. The dental implant as claimed in claim 1, wherein said first and second indexing elements are provided as radial projections which project from a surface of the fixture engagement portion of the dental component, and wherein said third and fourth indexing elements are provided as radial depressions in a surface of the component engagement portion of the dental fixture.

4. The dental implant as claimed in claim 1, wherein said at least two second indexing elements are asymmetrically distributed along the circumference of the fixture engagement portion with respect to the first indexing elements, and wherein said at least two fourth indexing elements are asymmetrically distributed along the circumference of the component engagement portion with respect to the third indexing elements.

5. The dental implant as claimed in claim 1, wherein a radius from a central axis of the fixture engagement portion to the centre of one of said at least two second indexing elements and a radius from said central axis to the centre of one of said two first indexing elements form a first angle $\theta$, wherein a radius from said central axis to another one of said at least two second indexing elements and said radius from said central axis to the centre of one of said first indexing elements form a second angle $\phi$, and wherein said second angle $\phi$ is different from said first angle $\theta$ and from any angle being a multiple of said first angle $\theta$, so that $\phi \neq n\theta$, where n is a positive integer.

6. The dental implant as claimed in claim 1, wherein the fixture engagement portion and the first and second indexing elements of the dental component are rotatable inside the component engagement portion of the fixture before the second indexing elements have mated the fourth indexing elements.

7. A dental implant comprising a dental component and a dental fixture, the dental component including:
- a fixture engagement portion for engaging a dental component with a dental fixture adapted to be inserted into a jawbone or for engaging the dental component with a fixture replica, the fixture engagement portion having a geometrical central axis and being provided with
  - at least two radially projecting first indexing elements, each having an apical end, the at least two radially projecting first indexing elements include a primary first indexing element and a secondary first indexing element being spaced from one another by a first cylindrical enveloping surface portion therebetween, and
  - at least two radially projecting second indexing elements being circumferentially spaced from one another and interposed circumferentially in the first cylindrical enveloping surface portion and between the primary first indexing element and the secondary first indexing element, each one of the second indexing elements having an apical end located further apically relative to the apical ends of said primary first indexing element and the secondary first indexing element, wherein the first cylindrical enveloping surface portion is free of additional radially protecting first indexing elements;

the dental fixture adapted to be inserted into a jawbone and comprising a component engagement portion adapted to mate with said fixture engagement portion, the component engagement portion being provided with
  - at least two third indexing elements having a coronal end, and
  - at least two fourth indexing elements being adjacent with one another, each one being radially spaced from the third indexing elements and having a coronal end located further coronally relative to the coronal end of said fourth indexing elements, wherein the first, second, third and fourth indexing elements are distributed along the circumference of the fixture engagement portion and the component engagement portion, respectively, in such way that the dental component can only mate in one rotational orientation with respect to the dental fixture, and wherein at least one of the two first indexing element is only enabled to mate with the third indexing element after said at least two second indexing elements have mated with said at least two fourth indexing elements.

8. The dental fixture as claimed in claim 2, wherein the fixture engagement portion includes a plurality of cylindrical enveloping surface portions, the plurality of cylindrical enveloping surface portions including the first cylindrical enveloping surface portion.

9. The dental fixture as claimed in claim 8, wherein each one of the at least two radially projecting first indexing elements are circumferentially spaced from one another by one of the plurality of cylindrical enveloping surface portions.

10. The dental fixture as claimed in claim 7, wherein the fixture engagement portion includes a plurality of cylindrical enveloping surface portions, the plurality of cylindrical enveloping surface portions including the first cylindrical enveloping surface portion.

11. The dental fixture as claimed in claim 10, wherein each one of the at least two radially projecting first indexing elements are circumferentially spaced from one another by one of the plurality of cylindrical enveloping surface portions.

* * * * *